(12) United States Patent
Lyndon

(10) Patent No.: US 12,414,872 B2
(45) Date of Patent: Sep. 16, 2025

(54) DEVICE FOR SUPPORTING A LOWER LIMB

(71) Applicant: ARTRA DESIGN PTY LTD, Valley Heights (AU)

(72) Inventor: Robert Lyndon, Valley Heights (AU)

(73) Assignee: ARTRA DESIGN PTY LTD, Valley Heights (AU)

( * ) Notice: Subject to any disclaimer, the term of this patent is extended or adjusted under 35 U.S.C. 154(b) by 366 days.

(21) Appl. No.: 17/912,210

(22) PCT Filed: Mar. 29, 2021

(86) PCT No.: PCT/AU2021/050278
§ 371 (c)(1),
(2) Date: Sep. 16, 2022

(87) PCT Pub. No.: WO2021/195696
PCT Pub. Date: Oct. 7, 2021

(65) Prior Publication Data
US 2023/0134809 A1    May 4, 2023

(30) Foreign Application Priority Data
Apr. 3, 2020    (AU) .............................. 2020901035

(51) Int. Cl.
*A61F 5/058*    (2006.01)

(52) U.S. Cl.
CPC .... *A61F 5/0585* (2013.01); *A61H 2201/0192* (2013.01); *A61H 2201/12* (2013.01);
(Continued)

(58) Field of Classification Search
CPC ...... A61H 2003/005; A61H 2201/0192; A61H 2201/12; A61H 2201/1652;
(Continued)

(56) References Cited

U.S. PATENT DOCUMENTS

| 3,942,521 A | 3/1976 | Klippel |
| 4,494,534 A | 1/1985 | Hutson |

(Continued)

FOREIGN PATENT DOCUMENTS

WO    1991/013604 A1    9/1991

OTHER PUBLICATIONS

International Search Report and Written Opinion dated Jun. 4, 2021, issued in corresponding International Patent Application No. PCT/AU2021/050278.
International Preliminary Report on Patentability dated Aug. 26, 2022, issued in corresponding International Patent Application No. PCT/AU2021/050278.

*Primary Examiner* — Alireza Nia
*Assistant Examiner* — Daniel A Miller
(74) *Attorney, Agent, or Firm* — Morgan, Lewis & Bockius LLP

(57) ABSTRACT

A device for supporting a lower limb of a subject. The device has a housing for a lower limb and a limb support. The housing has a longitudinal axis aligned with a longitudinal axis of the lower limb. A driving mechanism connected between the housing and the limb support, causes movement of the limb support between a retracted position parallel to the longitudinal axis of the housing and an extended position in which the limb support extends perpendicularly to the longitudinal axis of the housing to support the lower limb.

19 Claims, 11 Drawing Sheets

(52) U.S. Cl.
CPC ............... *A61H 2201/1652* (2013.01); *A61H 2203/0437* (2013.01)

(58) Field of Classification Search
CPC .... A61H 2201/1642; A61H 2201/1253; A61H 2201/165; A61H 2203/0437; A61H 3/00; A61F 5/0585; A61F 5/3761; A61F 5/0123; A61F 5/0127; A61F 5/013; A61F 5/37; A61F 5/01; A61F 5/0102; A61F 5/0125; A61F 5/0167; A61F 5/0158; A61F 5/02; A61F 5/30; A61F 5/0195; A61F 5/00; A61F 2005/0137; A61F 2005/0165; A61G 7/075; A61G 7/0755; A47C 7/50; A47C 16/00; A47C 16/02; A47C 16/025
USPC ............................................................ 602/23
See application file for complete search history.

(56) References Cited

U.S. PATENT DOCUMENTS

| | | |
|---|---|---|
| 4,837,873 A | 6/1989 | Dimatteo et al. |
| 5,300,016 A | 4/1994 | Marlatt |
| 5,547,464 A | 8/1996 | Luttrell et al. |
| 8,778,031 B1 * | 7/2014 | Latour, Jr. ............ A61F 5/0102 135/65 |
| 10,130,547 B2 | 11/2018 | Koren |
| 10,667,618 B2 * | 6/2020 | Distler ................. A61G 7/0755 |
| 2010/0100020 A1 * | 4/2010 | Fout ...................... A61F 5/0195 602/23 |
| 2017/0049240 A1 | 2/2017 | Miller |
| 2017/0360646 A1 | 12/2017 | Poli et al. |
| 2019/0070061 A1 * | 3/2019 | Choi ........................ A61H 3/00 |
| 2019/0274437 A1 * | 9/2019 | Distler ................. A47C 16/025 |

* cited by examiner

DEVICE FOR SUPPORTING A LOWER LIMB

FIELD OF THE INVENTION

The present invention relates to device for supporting a lower limb and in particular, to a device which can support a lower limb of a patient in an extended position of the lower limb, at a position elevated from the ground when the patient is seated.

The invention has been developed primarily for use while a patient is recuperating from an injury to a lower leg such as a fracture or surgery or other trauma and will be described hereinafter with reference to this application. However, it will be appreciated that the invention is not limited to this particular field of use.

BACKGROUND OF THE INVENTION

Typically, when a patient is recovering from surgery or other trauma such as a fracture in a lower leg, they are advised by a physician to elevate the injured lower leg to promote venous blood flow. Return of blood from lower extremities is inhibited by swelling of the lower limb. This is caused by interruptions to the vasculature by the trauma and the immune response to this trauma. There is typically a higher osmotic pressure in the tissues surrounding the veins than in the veins themselves which causes fluid to be drawn into the surrounding tissues.

The lower limb needs to be elevated relative to the heart of the patient to harness the force of gravity to assist venous return. When the patient is confined to bed, various supports can be used to elevate the lower limb. For example, the lower limb may be tired to a frame using one or more ties.

When a patient no longer requires bed rest, they are usually prescribed to wear a protective orthotic boot to protect the injured lower leg. The orthotic boot cushions the lower leg while providing mechanical stability to the lower limb.

Typically, after the patient is discharged from the hospital, they are still required to wear the orthotic boot for an extended period of time and also, to elevate their lower leg during the day, while recuperating.

The patient may use a stool or other type of furniture to rest their foot on while sitting. However, the stool must be the correct height to effectively elevate the limb and also, be comfortable to the user.

When the patient is not at home and a stool or other furniture at the right height is not available, the patient does not have a convenient option to elevate their limb.

If it is not convenient to elevate their lower limb while at home or outdoors, then the patient may not be motivated to stick to the prescribed therapy of elevating their lower limb. This may cause the patient to develop a significant amount of oedema in their lower limb and as a result, may take longer to recuperate and/or result in other medical problems.

The present invention seeks to provide a solution which will overcome or substantially ameliorate at least some of the deficiencies of the prior art, or to at least provide an alternative.

It is to be understood that, if any prior art information is referred to herein, such reference does not constitute an admission that the information forms part of the common general knowledge in the art, in Australia or any other country.

SUMMARY OF THE INVENTION

In an aspect of the present disclosure, there is provided a device for supporting a lower limb, comprising:

a housing for a lower limb, the housing having a longitudinal axis;
a limb support;
a pivoting mechanism connected between the housing and the limb support for, in use, pivotably moving the limb support from a retracted position substantially parallel to the longitudinal axis of the housing to an extended position in which the limb support extends substantially perpendicularly to the longitudinal axis of the housing to support the lower limb.

The pivoting mechanism may comprise a pivot about which the first end of the limb support may pivot to move between the retracted position and the extended position.

The pivoting mechanism may be a linear actuator. The linear actuator may be battery-operated.

In another aspect of the present disclosure, there is provided a device for supporting a lower limb, comprising:

a housing for a lower limb, the housing having a longitudinal axis aligned with a longitudinal axis of the lower limb, in use;
a limb support;
a driving mechanism connected between the housing and the limb support, the driving mechanism comprising a first part attached to the housing and a second part connected to the limb support;
wherein, in use, movement of the first part of the driving mechanism in a direction parallel to the longitudinal axis of the housing drives movement of the limb support between a retracted position parallel to the longitudinal axis of the housing and an extended position in which the limb support extends perpendicularly to the longitudinal axis of the housing to support the lower limb.

The housing may include a leg portion to house a leg of a subject.

The housing may include a foot portion to house a foot of a subject.

The foot portion may have a first side and an opposed second side.

The foot portion may have a convex bottom surface. The convex bottom surface may comprise gripping material.

The foot portion may include a stabilizing portion extending from the bottom surface. The stabilizing portion may be configured to keep the device upright when the user is not wearing the device.

The stabilizing portion may be wedge shaped. The stabilizing portion may be configured to be compressible underfoot when the user is wearing the device.

The foot portion may include shock absorbent material. The shock absorbent material may be a relatively dense sponge.

The housing may include at least two rigid arms, each arm attached to each side of the foot portion to support the limb, in use.

The housing may include adjustable straps to secure a lower leg of the subject within the housing.

The housing may include a supporting cover that covers a substantial part of the back of the lower leg of the subject, in use.

The supporting cover may be attached to each of the at least two rigid arms.

The supporting cover may be adjustable to accommodate for different sizes of lower limb of a subject.

The limb support may comprise an elongated brace, the elongated brace may extend from a first end to a second end.

The limb support may comprise a base pivotally connected to the elongated brace.

The limb support may include an elongated brace and a base. The base may be pivotably connected to the elongated brace.

The limb support may further comprise a base lock to lock the base in a position substantially perpendicular to the elongate brace when the limb support is in the extended position.

The device may further include a fastener connected between the limb support and the housing to fasten the limb support to the housing when the limb support is in the retracted position. The fastener may be a release buckle.

The base may include two feet. Each of the two feet may have a convex lower surface. The convex lower surface may comprise a gripping material. First ends of each of the two feet may be angled towards each other. Second, opposing end of each of the two feet may be angled away from each other.

The driving mechanism may include a pivoting arrangement. The driving mechanism may be a mechanical linkage. The driving mechanism may have a first part and a second part.

The driving mechanism may comprise a handle for a user to grip and move the first part of the driving mechanism in a direction parallel to the longitudinal axis of the housing.

The handle may be faceted or curved.

The handle may be located adjacent the top of the first part of the driving mechanism.

The handle may be detachably attached to the first part of the driving mechanism via a fastener. The fastener may be an over centre fastener.

The first part of the driving mechanism may comprise a first elongate member. The first elongate member may extend from a first end to a second end.

The second part of the driving mechanism may comprise a second elongate member extending from a first end to a second end. The second end of the first elongate member may be pivotably connected to the first end of the second, substantially elongate member.

The second elongate member may be fixedly connected to the housing. The housing may include a restraining plate attached to the side of the foot via which the second substantially elongate member may be fixedly connected to the housing at an attachment point adjacent the first end of the second elongate member.

The elongated brace may comprise a guide extending along at least part of a length of the elongated brace. The guide may include a cavity. The guide may include a longitudinal slot contiguous with the cavity.

The second part of the driving mechanism may include a roller attached to the second end of the second elongate member. The roller may be located within the cavity of the elongated brace and moveable along the guide of the elongated brace. The roller may be a polyurethane roller.

The device may further comprise a driving mechanism lock to prevent movement of the first part of the driving mechanism in the longitudinal direction of the leg portion of the housing when the limb support is in the extended position or in the retracted position.

The driving mechanism lock may comprise a box longitudinally extending along an inner surface of the first elongated member. The box may have a longitudinally extending internal cavity. The box may have a slot contiguous with the internal cavity.

A roller may be attached to an arm of the housing adjacent the box. The roller may be located inside the cavity. Movement of the first elongated member parallel to the arm, moves the roller within the cavity along the slot. The roller may be a polyurethane roller.

The driving mechanism lock may include a window located through one side of the box. The driving mechanism lock may also include a stopper that can be moved into the window. Moving the stopper into the window when the roller is located between the window and the second end of the cavity may prevent movement of the roller within the cavity.

When the driving mechanism lock is disengaged, when the handle is pulled by a user in the longitudinal direction of the leg portion of the housing, pivotable movement of the first part relative to the second part may be caused. This movement, in turn, may cause movement of the second end of the second elongate member along the guide.

The arms of the housing, limb support and driving mechanism may substantially comprise a lightweight metal. The lightweight material may be aluminium.

Other aspects of the invention are also disclosed.

BRIEF DESCRIPTION OF THE DRAWINGS

Notwithstanding any other forms which may fall within the scope of the present invention, embodiments of the invention will now be described, by way of example only, with reference to the accompanying drawings in which.

DESCRIPTION OF EMBODIMENTS

Figure 1:
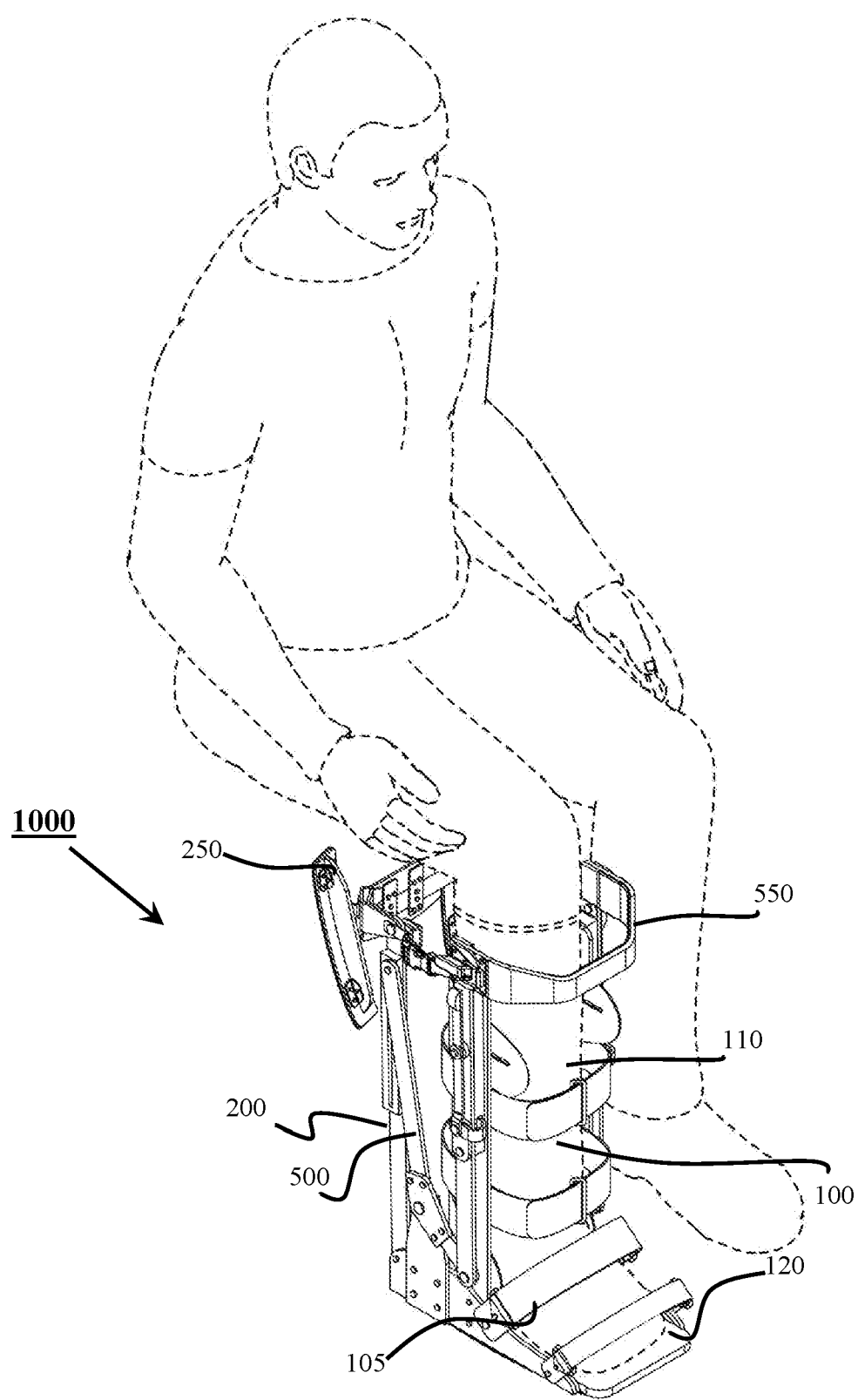
FIG. 1 illustrates a device for supporting a lower limb in accordance with an embodiment of the present invention, when the limb support is in the retracted position, in situ.

It should be noted in the following description that like or the same reference numerals in different embodiments denote the same or similar features.

A device for supporting a lower limb according to a first aspect of the invention is generally indicated by the numeral 1000. When a user of the device is seated on a bench or a chair, for example, and is wearing the device 1000 (as shown in FIG. 1), the device 1000 can be used to elevate the lower leg above the ground and also, to support the lower limb at a position above the ground when the knee is extended.

The device 1000 comprises a housing 100 for the lower limb. The housing 100 is substantially L-shaped and comprises a vertical leg portion 110 and a horizontal foot portion 120 which together also define an L-shaped cavity 130 configured to house the limb. The leg portion 110 has a longitudinal axis A which is substantially parallel to the longitudinal axis of the lower leg within the housing 100 when the device 1000 is worn by the user.

The device 1000 comprises a limb support 200 which is moveable between a retracted position (shown in FIG. 2) in which it is substantially parallel to the longitudinal axis of the leg portion of the housing 100, to an extended position (shown in FIG. 3) in which the limb support 200 extends substantially perpendicularly to the longitudinal axis of the leg portion of the housing 110.

The device 1000 comprises a pivoting arrangement between the housing 100 and the limb support 200 via which the limb support 200 is moveable between the retracted position and the extended position.

In an embodiment (not shown), the pivoting arrangement may include a pin or shaft attached to the housing and extending through an end of the limb support to allow the limb support to rotate relative to the housing and move between the retracted position and the extended position. It is envisaged that a number of different types pivoting arrangements may be used to move the limb support from the retracted to the extended position, in other embodiments.

In the illustrated embodiment, the device 1000 includes a driving mechanism 500 connected between the housing 100 and the limb support 200, which drives movement of the limb support 200 between the retracted position and the extended position. In the illustrated embodiments, this movement can be caused by force applied by the user to a part of the driving mechanism. In another embodiment (not shown), this movement can be caused by a motor or other type of driver.

In the illustrated embodiment, the driving mechanism 500 is a type of mechanical linkage. In an alternative embodiment, the driving mechanism 500 can include for example, a linear actuator or other driver. It is envisaged that a number of different driving mechanisms can be used in other embodiments.

Figure 2:
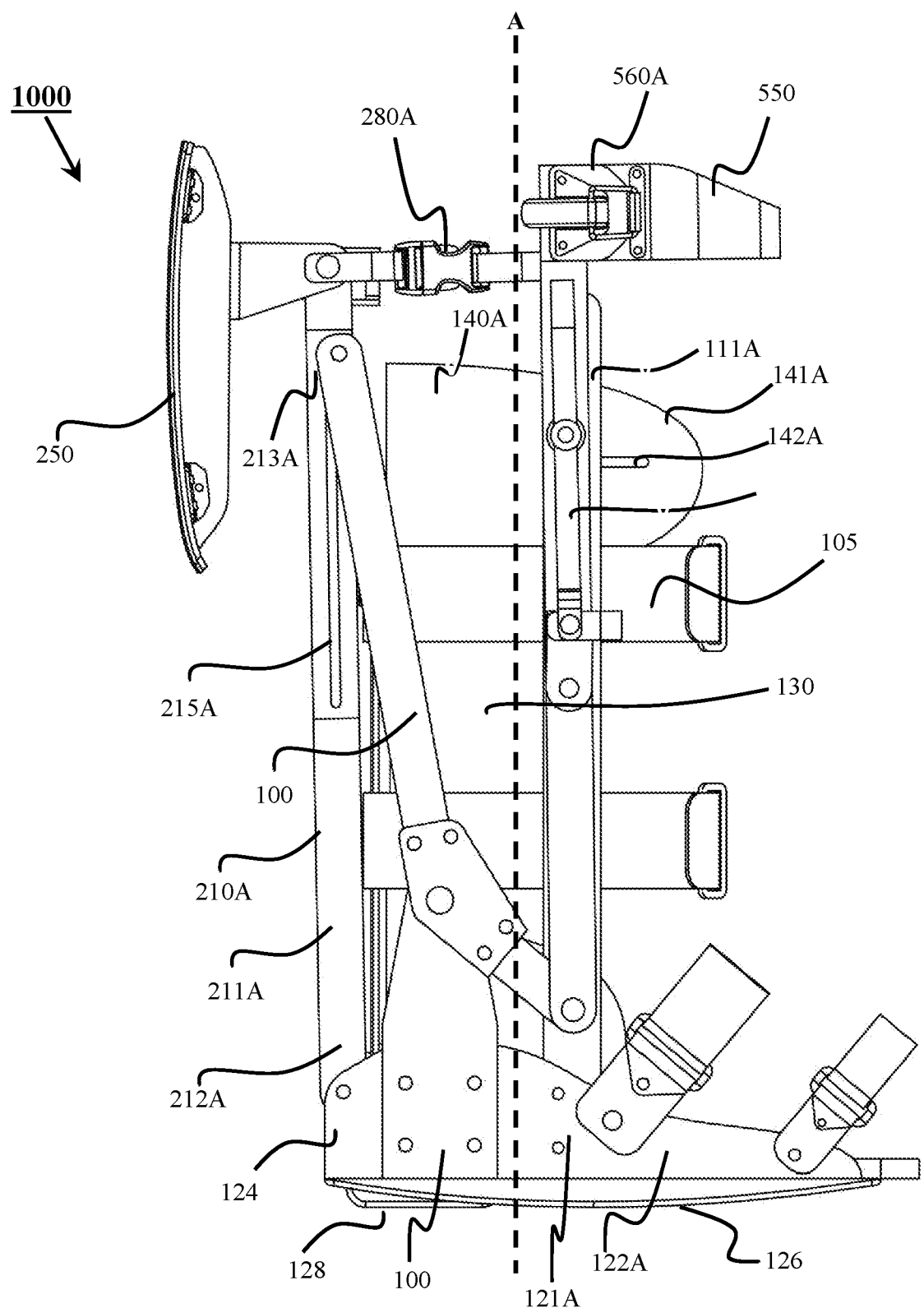
FIG. 2 is a side view of the device for supporting a lower limb in accordance with the embodiment of the present invention shown in FIG. 1.
Figure 4:
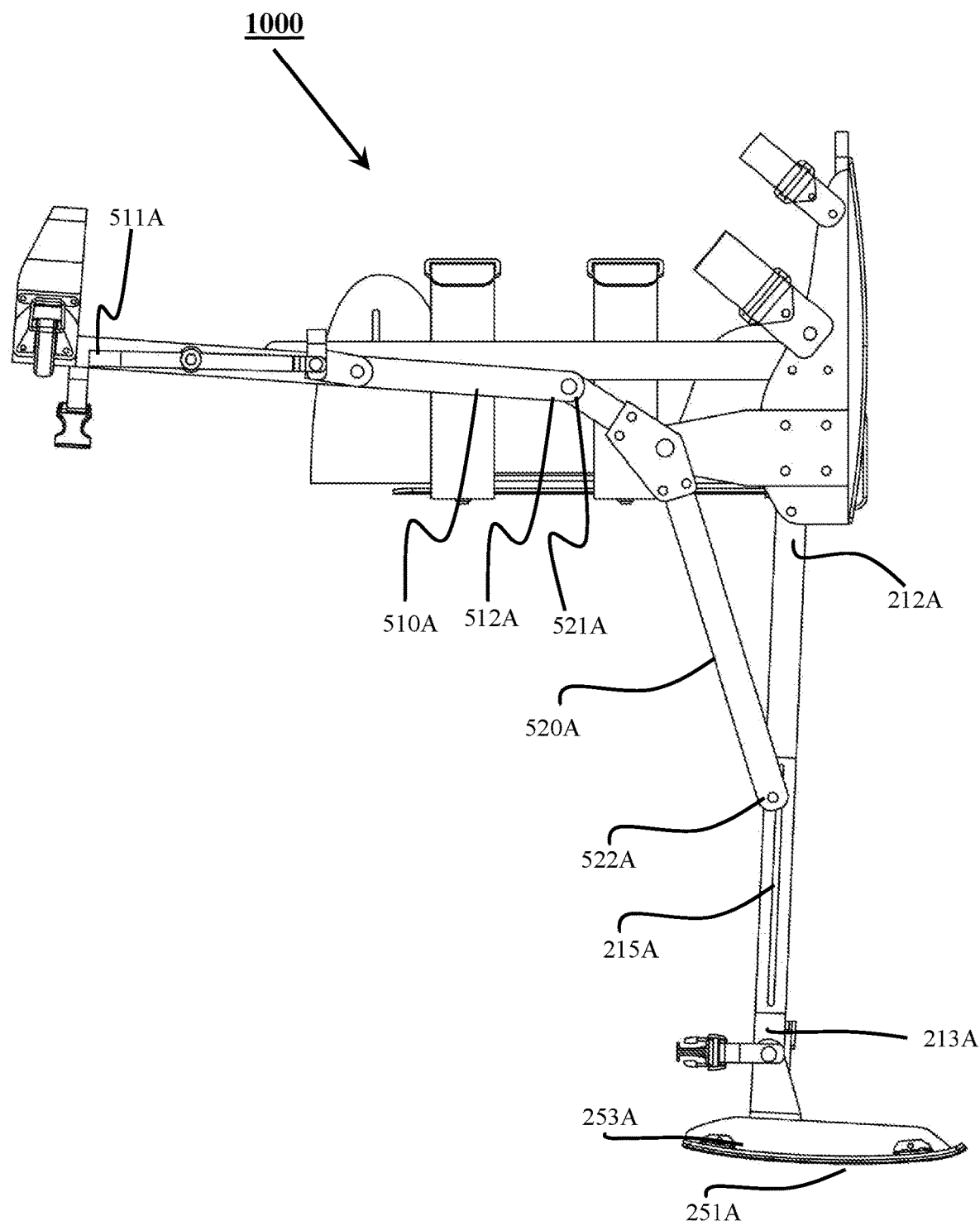
FIG. 4 is a side view of the device for supporting a lower limb in accordance with an embodiment of the present invention shown in FIG. 1 when the limb support is in the extended position.

FIG. 2 shows a seated user wearing the device 1000 when the limb support 200 is in the retracted position. FIG. 4 shows the user wearing the device 1000 when the limb support 200 is in the extended position.

The housing 100 is substantially L-shaped to accommodate the natural shape of a foot. As mentioned above, the housing 100 has a vertical component or a leg portion 110. The housing 100 also has a horizontal component or a foot portion 120. In this embodiment, the housing 100 is configured to house the lower leg of the patient while the patient wears an orthotic boot. In other embodiments, the housing 100 can be configured in size and shape to accommodate the lower limb of the patient while they are wearing normal shoes, or a plaster cast surrounding their lower limb, The foot portion 120 has a first side 121A and an opposed second side 121B. The foot portion 120 is configured to house the foot portion of an orthotic boot including the foot of the user of the device or subject.

The foot portion 120 is substantially rectangular. Each side of the foot portion 121A, 121B has a metal plate 122A, 122B to which various parts of the housing 100 are connected.

The leg portion 110 extends from the foot portion 120 to a position under the knee so when the patient is seated, the device 1000 is located below the knee as can be seen in FIG. 1.

As shown in FIG. 2, the leg portion 110 includes a first arm 111A extending vertically along the leg portion 120 from the first side of the foot portion 121A. The leg portion also includes a second arm 111B extending vertically along the leg portion 110 from the second side of the foot portion 120. The first arm 111A is opposed to the second arm 111B. An end of each arm is also fixed to the foot portion 120. Each of the first arm 111A and second arm 111B is sufficiently long to support the lower leg but does not extend pass the knee.

Figure 5:
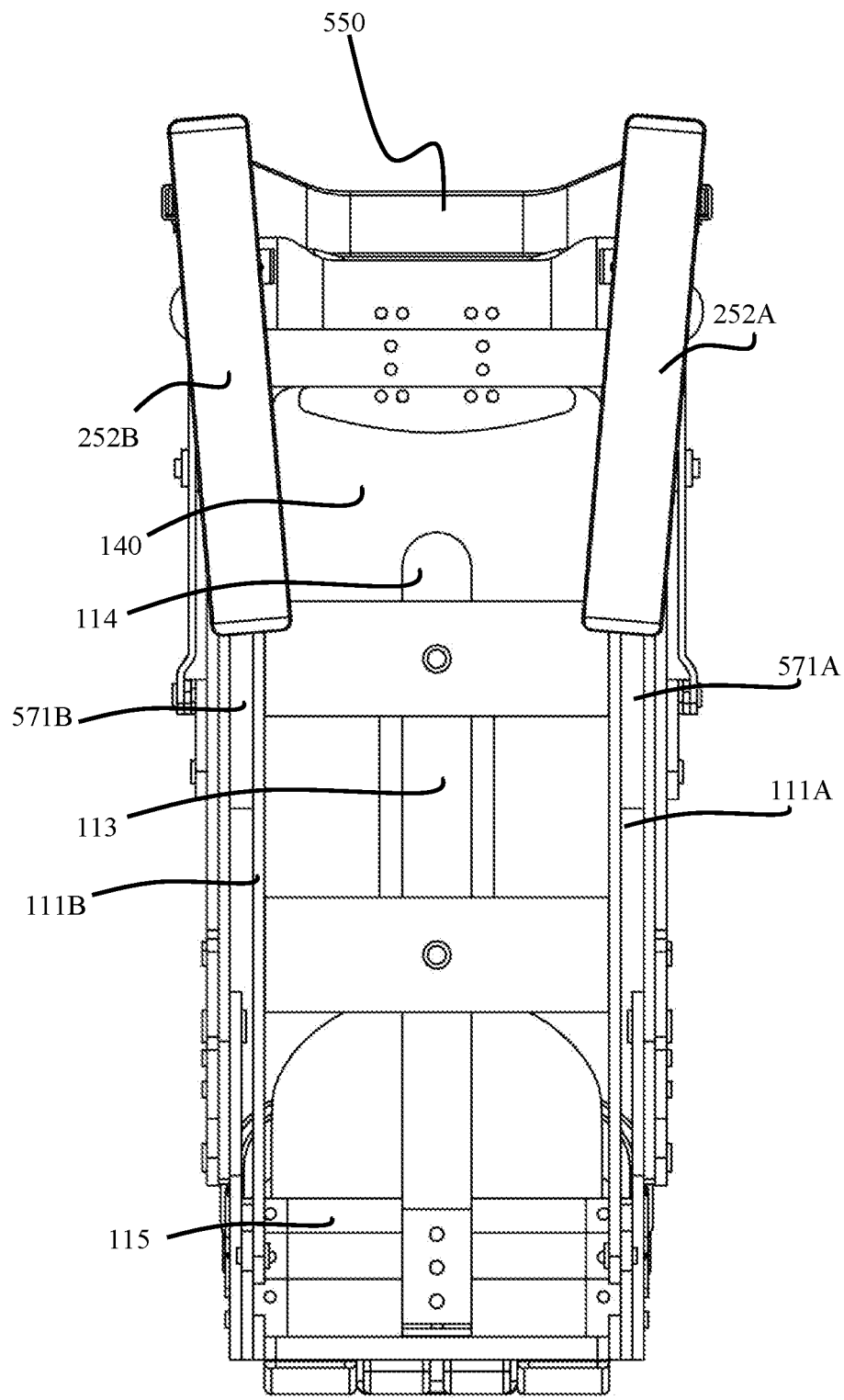
FIG. 5 is a back view of the device for supporting a lower limb in accordance with an embodiment of the present invention shown in FIG. 1.

FIG. 5 shows a back view of the device 1000 when the limb support 200 is in the retracted position. The leg portion 110 also includes a third arm 113 fixed to the back of the foot portion and extending vertically along the back of the housing to support the back of the lower leg of the user, in use. There is a plurality of horizontally extending braces 115, each of which are fixed to the first arm 111A, the second arm 111B and the third arm 113. They also connect the first arm 111A to the second arm 111B and located adjacent the rear of the foot portion 124. The braces mechanically support each of the first, second and third arms 111A, 111B, 113. In this embodiment, there are three braces, as shown in FIG. 5.

The third arm 113 extends partially up the back of the leg portion to a free end of the third arm 114. Advantageously, the third arm 113 is configured such that the free end of the third arm 114 can flex outwardly to accommodate a larger calf of a subject. In the illustrated embodiment, each arm is relatively flat and slender. In this embodiment, each arm is made of aluminium. Advantageously, aluminium is lightweight. In other embodiments, the arms may be made of the other materials.

Each of the leg portion 110 and the foot portion 120 of the housing comprises a plurality of adjustable straps 105 configured to secure the lower limb within the cavity of the housing. In the illustrated embodiment, each of the foot portion 120 and leg portion 110 have two straps spaced from each other. In the leg portion 110 of the housing, the straps extend circumferentially around the leg portion 110, over each of the three arms and are also secured to each of the three arms via screws. In the foot portion 120, each strap is connected across the foot portion to secure the foot of a user (including an orthotic boot) within the housing 100.

As can be seen in FIG. 2, for example, each end of each strap across the foot portion 120 is attached onto the metal plates 122A, 122B on either of the two sides of the foot portion 121A, 121B with screws. Each strap is configured such that it is adjustable via a hook and loop fastener and an adjustment loop.

In use, the user will typically be wearing an orthotic boot to protect and support the injured lower leg. Advantageously, the straps 105 are adjustable to accommodate a variety of different sizes of orthotic boots worn by user.

The housing further includes a supporting cover 140. The supporting cover 140 is configured to provide support to the limb within the leg portion of the housing and extends from the rear of the foot portion of the housing 124 to adjacent the underside of the knee. The supporting cover 140 is configured to at least partially cover substantially the whole length of the back of the leg. The supporting cover 140 is located internal to the three arms. The supporting cover 140 is fixed to the back of the foot portion 120 using screws.

In other embodiments, the supporting cover can be printed with a pattern or with drawings and be coloured in different colours. This may assist in the psycho-emotional aspect of recovery, especially when it The supporting cover 140 has two wings 141A, 141B that extend from the back of the supporting cover to wrap partially around either side of the lower leg of the subject, in use. Each wing 141A, 141B is located near the top of the leg portion adjacent a calf of a lower leg, when the device is worn by a user. Each wing 141A, 141B also comprises a slot 142A, 142B. Each of the first and second arms 111A, 111B has an internally facing screw which engages with each respective slot of the first and second wings 142A, 142B. The diameter of each screw head is larger than the width of each slot to retain the supporting cover. The supporting cover 140 is moveable relative to each of the first and the second arms 111A, 111B within the constraint of the length of each slot 142A, 142B to accommodate for different sizes of lower limb so that the patient can comfortably wear the device 1000.

The supporting cover 140 may be made of a sheet of tough plastic or fabric which is flexible but can substantially retain its shape while providing support to the lower limb, in use. User can The foot portion, in use, is configured to support the driving mechanism and the leg portion of the housing as well as the lower limb of the user.

In this embodiment, the foot portion of the housing 120 includes a core made of plywood. Advantageously plywood is a lightweight material. In other embodiments, the core may be made of other lightweight material. Metal angle brackets fix ends of each of the first, second and third arms 111A, 111B, 113 to the core using screws. Each of the metal side plates of the foot 122A and 122B are also fixed to the core using screws.

The foot portion 120 also includes padding of a dense foam. In particular, the plywood is covered with or encased within a dense foam. The padding acts to reduce any impact on the bones of the injured limb during load bearing by cushioning the foot of the user, in use. In other embodiments, the food portion may have more padding for example where the user is not wearing a cam boot and is bare foot for example. In yet other embodiments, where there is already sufficient support provided by an orthotic boot, less padding may be needed in the foot portion of the housing 120.

The foot portion 120 includes a padded sole 125 which will be in contact with the underside of the orthotic boot worn by the user, in use.

Figure 7:
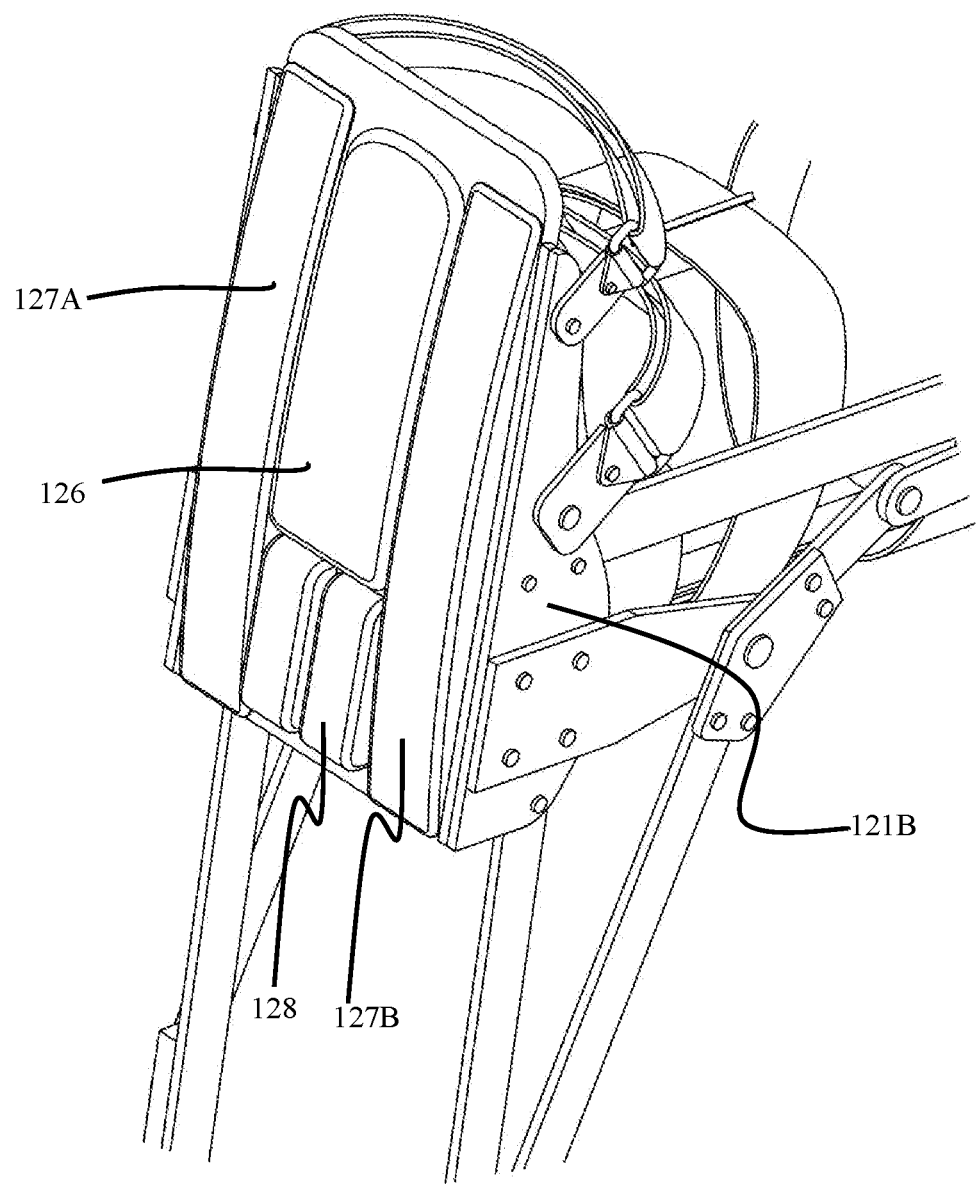
FIG. 7 is a perspective view of the device for supporting a lower limb in accordance with an embodiment of the present invention shown in FIG. 1.

As can be seen in FIGS. 2, 4 and 7, the underside of the foot portion 126 has a convex curvature. This prevents the instance of any force concentrations in areas of the injured foot, particularly when the user is wearing the device 1000 when the limb support 200 is in the retracted position while the user is seated. This also prevents jarring of the bones of the foot or lower leg when the underside of the foot portion 1000 contacts the ground when the device is worn by the patient. This will reduce the chance of the user experiencing pain while wearing and walking with the device 1000.

As mentioned above, the plywood is encased in relatively dense sponge. The dense sponge located between the plywood and strips is sufficiently shock absorbent to cushion the heel during heel-strike and improve comfort for the user. It is envisaged that in other embodiments, other types of shock-absorbent material can be used.

The underside of the foot portion also includes two grip strips 127A, 127B each extending longitudinally along the underside of the foot portion. In the illustrated embodiments one strip 127A is located adjacent the first side of the foot portion 121A and the other strip 127B is located adjacent the second side of the foot portion 121B. In this embodiment, the grip strips 127A, 127B are made of rubber and comprise a gripping pattern (not shown) to better engage with the ground to prevent the user slipping while wearing the device.

The foot portion 120 also includes a stabilising portion 128 which in the illustrated embodiments has a wedge shape and projects outwardly from the underside of the foot portion 120. The stabilising wedge 128 acts to prevent the device 1000 from tipping and falling over due to gravity when it is placed on a flat surface in an upright position such as on the ground. Hence, as the underside of the foot portion 126 is curved, the greatest height of the wedge is located near the rear edge of the foot portion. This can be seen in FIG. 2 for example.

A resiliently flexible member (not shown) attaches the stabilising wedge 128 to the underside of the plywood. In the illustrated embodiment, the resiliently flexible member is a simple spring.

The limb support 200 includes a base 220. In the illustrated embodiment, the base of the limb support 220 is relatively heavy and in a retracted position of the limb support 200, is located near the top of the device 1000. The stabilising portion 128 and spring are together configured to counterbalance the force of gravity on the top of the device that can act to tip the device over.

The stabilizing wedge 128 is made of a relatively soft sponge that is compressible underfoot such as when the user is walking while wearing the device. The spring is configured such that when the device 1000 is not loaded by the user, it is in its initial, extended position. Therefore, the spring is sufficiently resilient to remain in its extended position when the device 1000 is in an upright and retracted configuration. The spring is sufficiently flexible such that when the device is loaded by the user wearing the device 1000 and walking with the device 1000, the spring and stabilizing wedge 128 compress underfoot.

Thus, the stabilising wedge 128 makes it easier for the user to grip and put on the device 1000 without the inconvenience of the device falling over when the holder is not holding the device 1000. When the user is seated, it might be difficult to reach over and grab the device 1000 if it has fallen down. Especially, as the user is required to be careful when moving so as not to unnecessarily load the injured limb as this may cause pain. In the illustrated embodiments, the stabilising wedge 128 is located at the rear of the underside of the foot portion between the two grip strips 126.

The convex shape of the underside of the device 126, is configured for gradual load transfer when the user walks while wearing the device. During normal gait, the rear of the foot portion 124 will typically be loaded first and then load will be transferred along the length of the foot portion 120. The stabilising wedge 128 is made of relatively soft sponge to cushion the foot of a patient. The sponge is sufficiently thick and otherwise configured such that there is no gap between the sponge and surrounding outer surface of the foot portion to prevent small rocks and other sediment or soil, for example, getting stuck between the sponge and the plywood.

In other embodiments, the housing 120 can comprise padding to make the device more comfortable to wear. This will enable the user to use the device while wearing a thinner or less robust orthotic boot. In yet another embodiment, the user may be able to use the device without wearing an orthotic boot. In this case, the orthotic boot may be incorporated within the cavity of the housing to support the injured lower leg.

As mentioned above, the limb support 200 is moveable from the retracted position to the extended position, and vice versa.

The limb support 200 comprises an elongated brace 210 to support the lower limb above the ground in an extended position of the lower limb, in use. As shown for example, in FIGS. 1 and 2, the elongated brace 210 is located external to and at the rear of the housing 100 when the limb support 200 is in the retracted position.

The elongated brace 210 is sufficiently strong and stable to support the lower limb when the knee is extended.

The total height of the limb support 20 is selected to ensure that when the limb support is in the extended position, that the lower limb is substantially perpendicular to the limb support 200 when the device 1000 is worn. If the limb support 200 is too high then there may be unnecessary forces applied to parts of the lower limb such as the hip which may make the user uncomfortable.

In another embodiment (not shown), the limb support may be at a height at which the lower limb is not perpendicular to the limb support in use while being comfortable for the user.

In another embodiment (not shown), the limb support may have an adjustable height. It is envisaged that the skilled person will be able to make the height of the limb support adjustable in a number of different ways.

The elongated brace 210 comprises two slender arms 211A, 211B spaced horizontally from each other and located on either side of and at the rear of the housing 100 when the limb support 200 is in the retracted position. In the retracted position, each arm of the elongated brace 211A, 211B extends vertically from the rear of the foot portion of the housing 124. Each arm 211A, 211B is pivotably connected to the rear of the foot portion of the housing 124. Each arm has a first end 212A, 212B and a second end 213B, 213B.

Each arm 211A, 211B also includes a guide 215A, 215B to guide the movement of the limb support 200 between the retracted and the extended position. Each guide 215A, 215B is a slot longitudinally extending along the length of each of the two arms of the elongated support 211A, 211B. Each arm 211A, 211B has an inwardly facing side facing the housing and an outwardly facing side facing away from the housing. In the illustrated embodiment, each slot is located on the outwardly facing side and extends from adjacent the base 250 or near the second end of each arm 211B, 212B to approximately halfway along the elongated support 210.

Each second part of the driving mechanism 520A engages with each respective slot (as explained in detail below). The length of each slot is configured to allow the second part of the driving mechanism 520B to move relative to the slot and cause the limb support 200 to move between the retracted position and the extended position. Each slot restrains the second part of the driving mechanism 520A and controllingly guides the movement of the limb support 200 into the extended position or the retracted position.

The second end of the each of the arms 213A, 213B are pivotably connected to the base 250 such that the elongated brace 210 can be moved from a reduced position in which the base 250 is substantially parallel to the elongate brace 210 to a position in which the base is perpendicular to the elongate brace 210 for supporting the lower limb in the extended position of the limb support 200.

The device 1000 includes a base lock 400 to lock the base 250 in a position perpendicular to the elongated brace 210.

Advantageously, the base 250 can be folded behind the housing 100 in the reduced position as shown in FIG. 2 so as not to obstruct the user while the user is moving. This also results in a relatively compact and sleek device.

Figure 6:
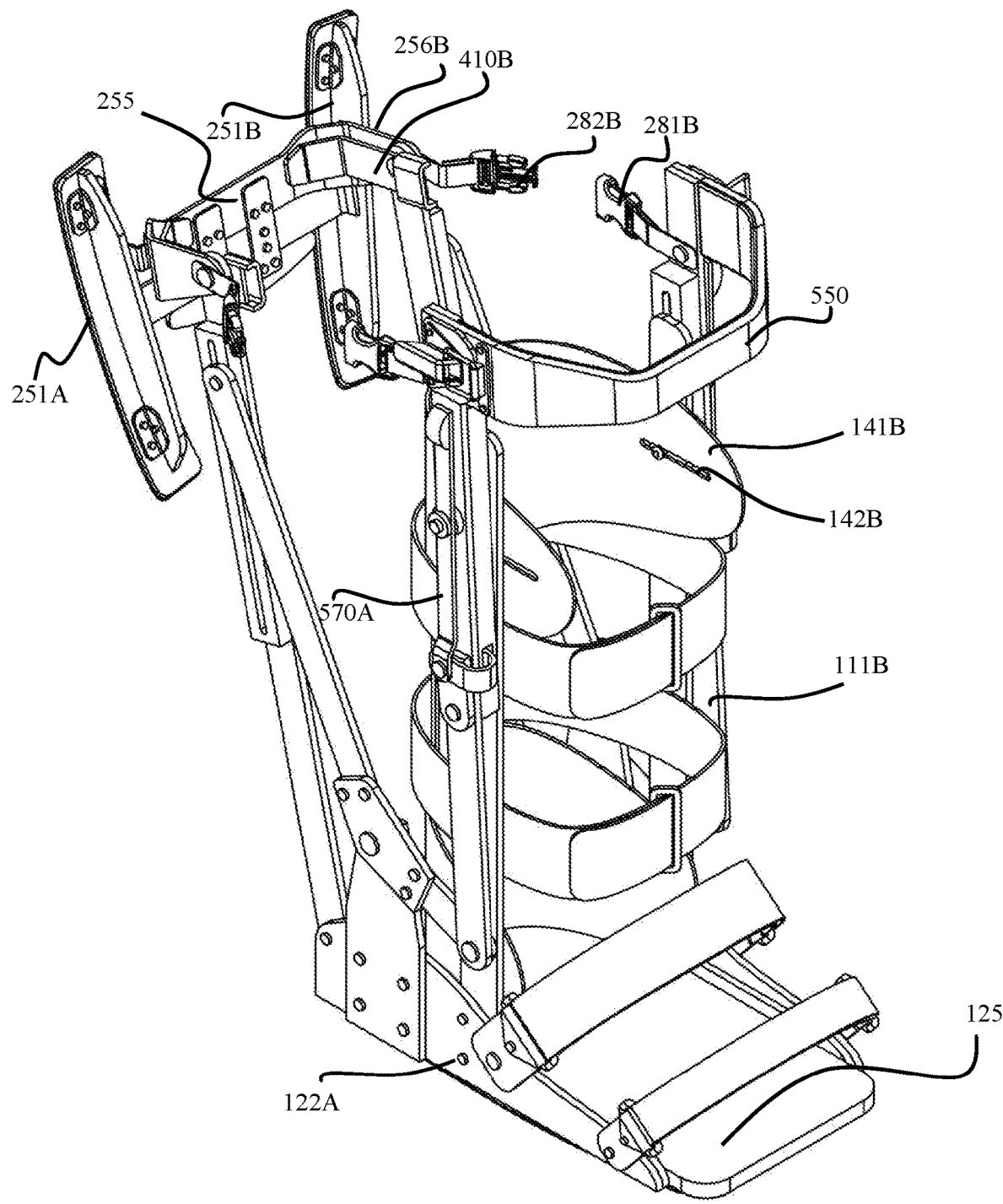
FIG. 6 is a view of the underside of the housing of the device for supporting a lower limb in accordance with an embodiment of the present invention shown in FIG. 1.

As can be seen in FIG. 6, the base 250 also includes a pair of curved feet 251A, 251B, adjacent each other and spaced horizontally from each other. Each foot 251A, 251B has a convex outer surface 252A, 252B for contacting the ground that is covered with a gripping material. The gripping material comprises a tread (not shown) for engaging with the ground when the outer surface of each of the feet 252A, 252B are in contact with the ground when the limb support 200 is in the extended position.

As shown, for example, in FIG. 5, when the limb support 200 is in the retracted position and the base 250 is in a position parallel to the limb support 200, the upper ends of the feet 257A, 257B are turned outwardly while the lower ends of the feet 258A, 258B are angled inwardly. Advantageously, this is so that the upper ends of the feet 257A, 258B do not protrude into the thigh of the subject when the subject is wearing the device and seated, and the limb support 200 is in the retracted position.

Another advantage of this is that when the limb support 200 is in the extended position, the outwardly angled nature of the feet 251A, 251B reduces the likelihood of the base 250 from slipping backwards or forwards when the subject moves compared to if the feet were parallel to each other. There is greater surface area of contact between the sides of the feet and the ground when the feet are outwardly angled compared to when they are parallel to each other. This increases the friction between the ground and each of the feet.

A flange 253A, 253A extends perpendicularly from approximately the centre of each of the feet 257A, 257B. As shown in FIG. 6, the two curved feet are connected to each other by a bridge 255 fixed to each of and extending between the two flanges 253, 254.

The bridge 255 has a substantially rectangular portion extending between the two flanges. The bridge 255 also has two end portions 256A, 256B extending substantially perpendicularly from either side of the rectangular portion. Each of the two end portions 256A, 256B is pivotably connected to a respective second end of a respective arm of the elongated brace 213A, 213B with a suitable fastener. It is envisaged that a number of known fasteners can be used to pivotably attach each end portion 256A, 256B to the respective second end of an arm of the elongated brace 213A, 213B.

As mentioned above, the limb support 200 comprises a base lock 400 to lock the base in a position substantially perpendicular to the elongate brace when the limb support is in the extended position. In use, when the base lock 400 is disengaged, the user can grip the bridge 255 to rotate and move the base about the second end of the elongated support.

The base lock 400 has two identical parts 400A, 400B located internal to each end portion of the bridge 256A, 256B. Each part of the base lock comprises a lever 410A, 410B each having a first end 411A, 411B, and a second end 412A, 412B and a resiliently flexible member 450A, 450B.

Figure 8:
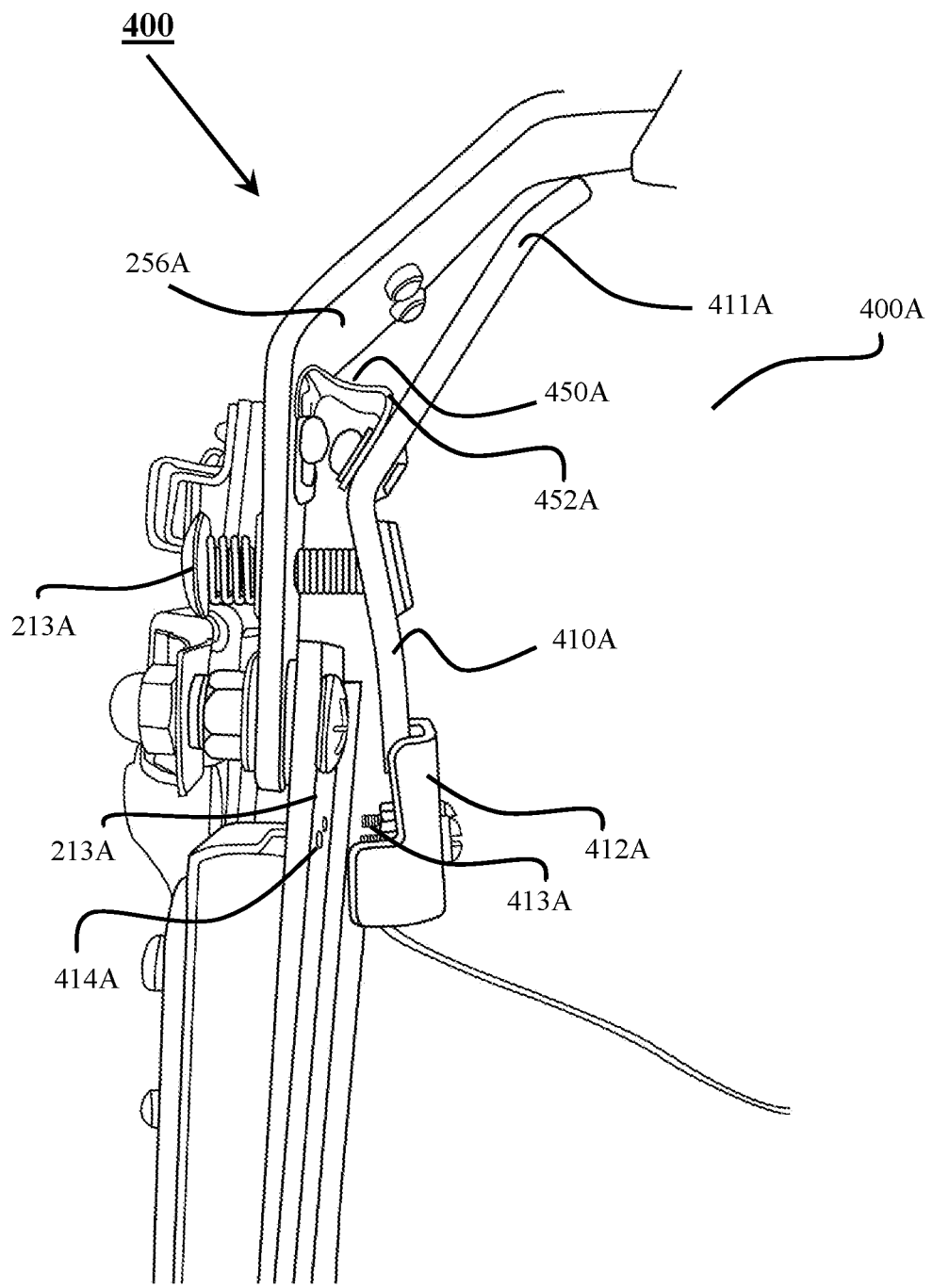
FIG. 8 is a partial view of base lock for supporting a lower limb in accordance with an embodiment of the present invention shown in FIG. 1.
Figure 9:
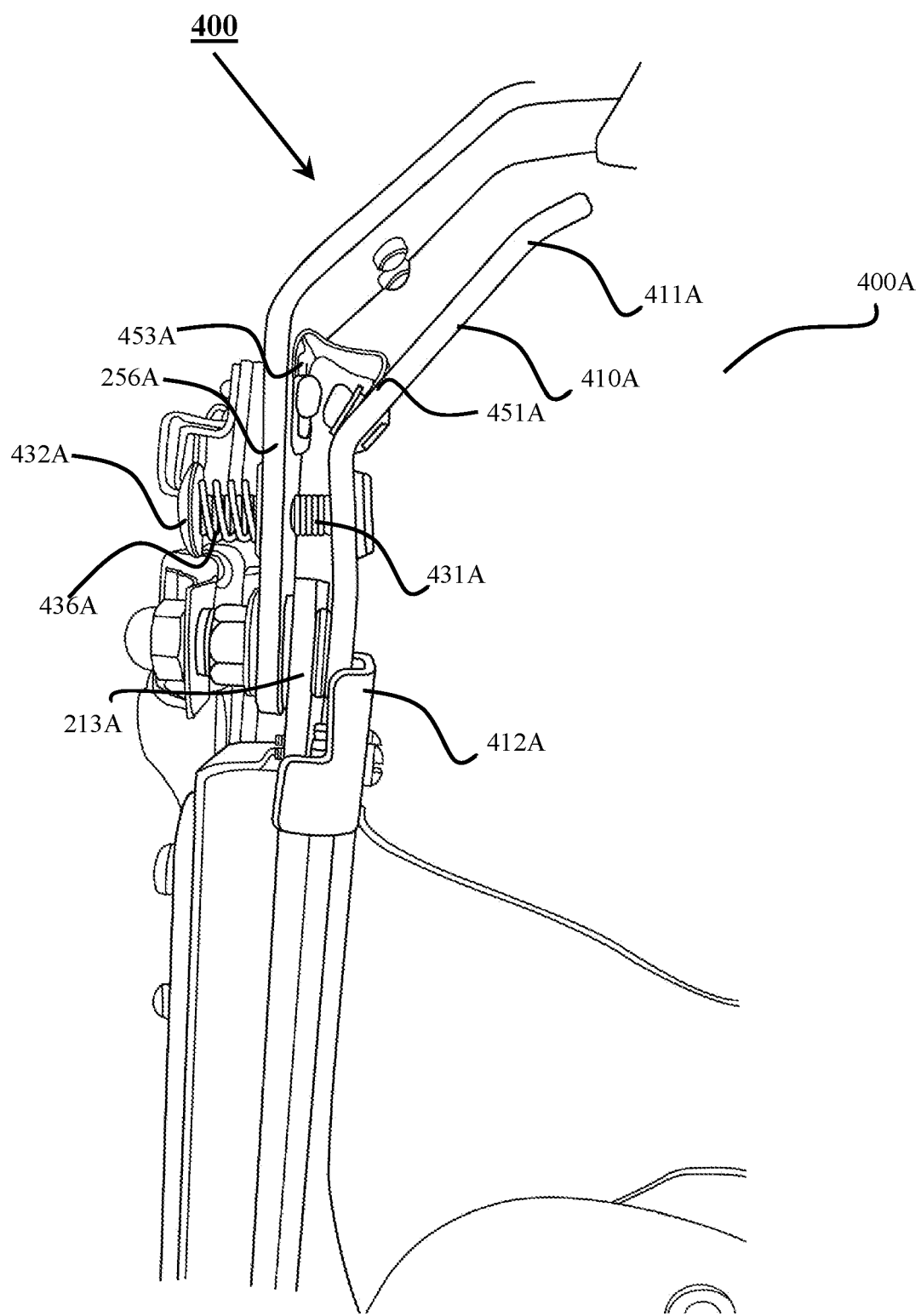
FIG. 9 is another partial view of the base lock for supporting a lower limb in accordance with an embodiment of the present invention shown in FIG. 1.

FIGS. 8 and 9 depict one side of the base lock 400A, the resiliently flexible member 450A is located between and fixed to each of the lever 410A and the respective end portion of the bridge 256A. The resiliently flexible member 450A provides a fulcrum 452A about which the lever pivots to move a second end of the lever 412A. Applying a force at a first end of the lever 411A to move the first end of the lever towards the adjacent perpendicular portion of the bridge 256A, moves the second end of the lever 412A away from the second end of the respective arm of the elongated member 213A. This is illustrated in FIG. 8.

The lever 410A can be made of a suitable metal such as aluminium and steel and is rigid. The lever 410 is shaped to follow part of the shape of the inner surface of the bridge as shown in FIG. 9, so as not to protrude into the cavity of the housing 130, in use.

The first end of the lever 411A is sufficiently wide to allow a user to comfortably push the first end of the lever 411A down with their thumb.

Each part of the base lock 400A also includes two screws 413A extending through and fixed to the second end of the lever 412A. As shown in FIG. 9, the bodies of the screws extend in a direction towards the second end of the respective arm of the elongated member 213A.

When the base 450 is in the perpendicular position, each screw 413A is aligned with a respective one of two holes 414A extending through the second end of the respective arm of the elongated member 213A.

Each hole 414A is configured to receive and retain a substantial portion of the bodies of each screw to prevent the base 250 moving out of the perpendicular position.

The resiliently flexible member 450 is attached to the lever 410A at a position approximately midway between the first end 411A and the second end of the lever 412A. The resiliently flexible member 450A is a thin sheet of metal bent to define three planar parts. A first planar part 451A is fixed to the perpendicular portion and an opposed third planar part 453A is fixed to the lever and a second planar part extending between the first and the third parts. There is bend between the second and the third parts. The second bend acts as the fulcrum 452A about which the lever 410A pivots.

The base lock 400A also includes a restraint 430A which locates the lever 410A relative to the inner surface of the bridge 255, prevents lateral movement of the lever 410A. The restraint 430A also acts to control the movement of the second end of the lever 412A when the first end of the lever 411A is depressed by the thumb of the user.

The restraint 430A comprises a screw having a body 431A extending from a head of the screw 432A located external to an outer surface of the respective end portion of the bridge 256A, through the respective end portion 256A, between the respective end portion 256A and the lever 410A and through the lever 410A to an outer surface of the lever 410A. The end of the body of the screw is fixed to the lever 410A such that the lever 410A cannot move along the body of the screw 431A.

The head of the screw 432A is spaced from the outer surface of the respective end portion by a helical spring 436A around the part of the body of the screw that is external to the respective end portion of the bridge 256A.

The spring 436A is biased to prevent any movement of the head 432A towards the end portion and ensure that the two screws of the second end of the lever 412A are retained within the holes in the second end of the elongated member 414A, in the absence of any user-applied forces on the first end of the lever 411A.

To unlock the base 250 from an engaged position of the lock 400, as shown in FIG. 9 the user can simultaneously press on both levers 410A, 410B until the screws are moved out of the holes as shown in FIG. 9. This movement releases the base 250 from the second end of the respective arm of the elongated brace 213A and the user can move the base 250 into the position parallel to the elongated member.

In other embodiments, it is envisaged that other types of locks can be used to lock the base to the elongated brace.

As mentioned above, the driving mechanism 500 drives the movement of the limb support 200 from the retracted position to the extended position. In the illustrated embodiment, the driving mechanism 500 is a type of mechanical linkage. In another embodiment (not shown), the driving mechanism 500 can include a battery-operated linear actuator that is actuated by a button. It is envisaged that a number of different driving mechanisms can be used to drive the limb support 200 between the retracted position and the extended position. The driving mechanism 500 includes a pivot about which the limb support 200 rotates relative to the housing 100.

The driving mechanism 500 as shown in the illustrated embodiments extends between the limb support 200 and the arms 111A, 111B of the leg portion of the housing on either side of the device. The driving mechanism and has a first side 500A and an identical second side 500B.

The first side of the driving mechanism 500A includes a first part 510A and a second part 520B and is connected to a first arm of the elongated support 211A. The second side of the driving mechanism 500B also includes a first part 520A and a second part 520B and is connected to the second arm of the elongated brace 211B. In this way, each side 500A, 500B of the driving mechanism 500 separately and simultaneously drives the respective side of the limb support that it is connected to.

The first part of the driving mechanism 510A is a first elongate member extending from a first end 511A to a second end 512A. The second part of the driving mechanism 520A comprises a second substantially elongate member which also extends from a first end 521A to a second end 522A. The second end of the first elongate member 512A is pivotably connected to the first end of the second elongate member 521A.

There is a polyurethane roller (not shown) attached to and extending from the surface of the second end of the second elongate member 522A that is facing the slot of the guide 215A. The arm of the elongated support includes a longitudinally extending internal cavity and a slot 215A contiguous with the internal cavity.

The polyurethane roller is seated within the internal cavity of the elongated support of the limb support and is configured to move along the length of the slot 215A and therefore, allow the limb support to move between the retracted and extended positions.

As mentioned previously, the driving mechanism 500 is configured such that pivotable movement of the first part 510A relative to the second part 520A causes movement of the second end of the second elongate member along the guide.

The driving mechanism 500 also comprises a handle 550 attached between and connecting the two sides of the driving mechanism. In particular, the first part of the driving mechanism comprises a handle 550 for a user to grip and move the first part of the driving mechanism in a direction parallel to the longitudinal axis of the leg portion of the housing 110.

As mentioned previously, movement of the first part of the driving mechanism 510A in a direction parallel to the longitudinal axis of the leg portion of the housing 100 drives movement of the limb support 200 between a retracted position parallel to the longitudinal axis of the housing and an extended position in which the limb support extends perpendicularly to the longitudinal axis of the housing to support the lower limb.

The handle 550 also extends from a first end 551A to a second end 551B. The handle 500 projects outwardly from the housing 100. The handle 550 is also faceted such that there is enough space between the handle 550 and the lower limb for the user to insert their fingers under the handle 550, grip and move the handle 550 to drive movement of the limb support 200. In another embodiment (not shown), the handle 550 can be curved with a convex inner surface facing the limb of a user, in use.

The handle 550 is also detachable from the first part 510A of the driving mechanism.

The handle 550 has an outer surface and an inner surface. FIG. 2 shows each end of the handle 551A, 551B is engaged with and attached to the respective first part of each side the driving mechanism 510A, 510B via a respective fastener 560A, 560B. In this embodiment, the fastener 560A, 560B is a type of over-centre fastener with a catch plate or "mousetrap" fastener.

Figure 10:
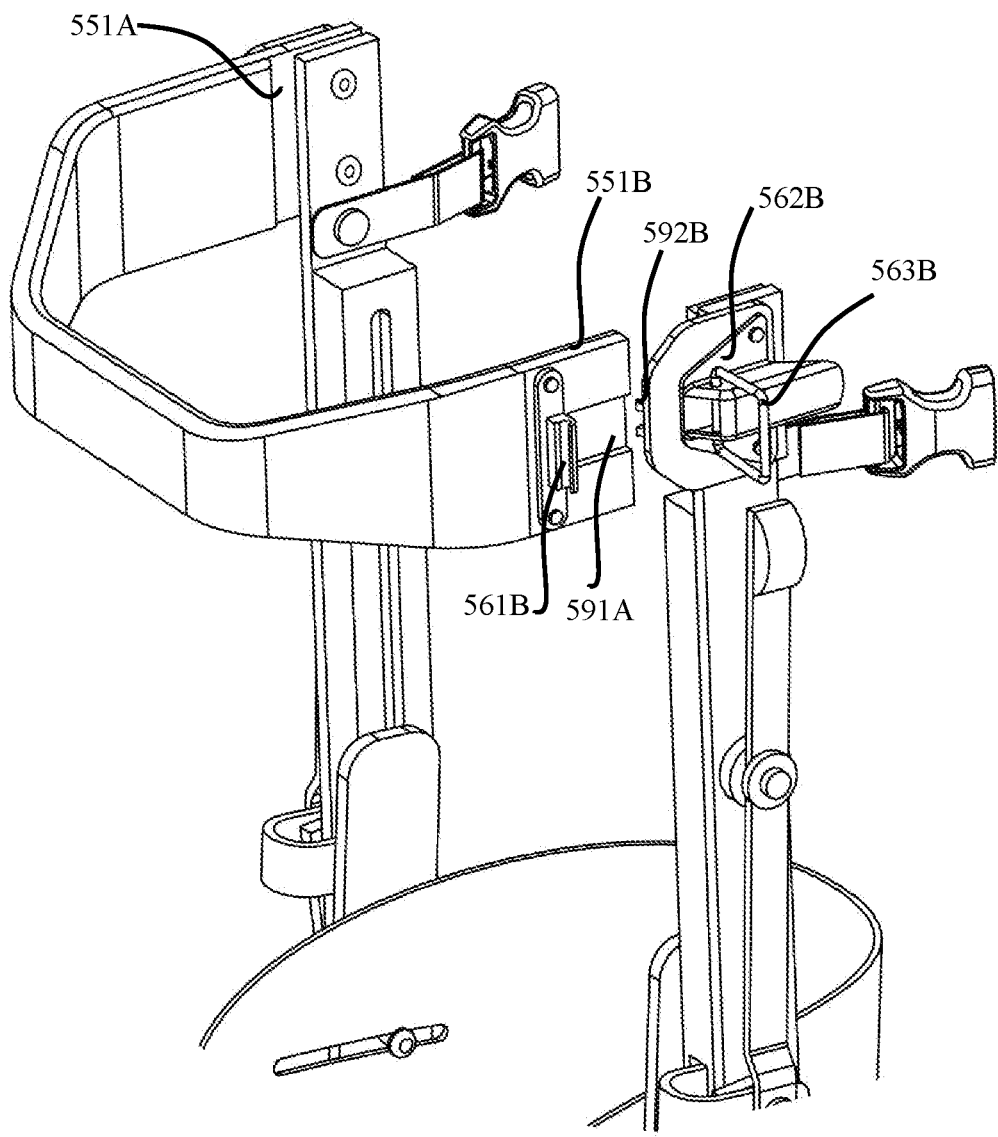
FIG. 10 is view of the top end of the device in accordance with an embodiment of the present invention shown in FIG. 1.

FIG. 10 illustrates the fastener 560B. The catch plate 561B of the fastener 560B includes a curved retainer configured to engage with and retainingly hold a loop 563B attached to a body of over-centre fastener 562B. The catch plate 561B is fixed to the outer surface of the handle and adjacent the end of the handle 551B.

The body of the over-centre fastener 562B is attached to an outer side of the top of the second arm of the driving mechanism 511B and includes a loop 563B to engage with the retainer.

The handle 550 and the top end of each side of the first elongate member of the driving mechanism 511B, 511A together also include an alignment guide 590A, 590B to correctly align each catch plate 561A, 561B with the body of the over centre fastener 562A, 562B, such that each loop of the body of the over centre fastener 563B, 563A can easily engage with the catch plate and the end of the handle 551A, 511B and top end of the first part provide a smooth surface adjacent the limb, in use, when the handle is connected to the first part of the driving mechanism.

The alignment guide 590A has a female part or recess 591A located under the catch plate. The alignment guide 590A also has a male part 592A configured to receive the female part 591A when the first and second parts of the alignment guide are brought together. The male part 592A is located under the body of over-centre fastener 562A, 562B.

The second substantially elongate member 520A, 520B of the driving mechanism 500A, 500B has a first portion 523A, 523B that extends out of longitudinal alignment with the second portion 524A, 524B. There is a bend defined between the two portions 525A. It is envisaged that in other embodiments, the first portion will be in longitudinal alignment with the second portion i.e. the second substantially elongate member 520A, 520B will be a single elongate member.

Figure 3:
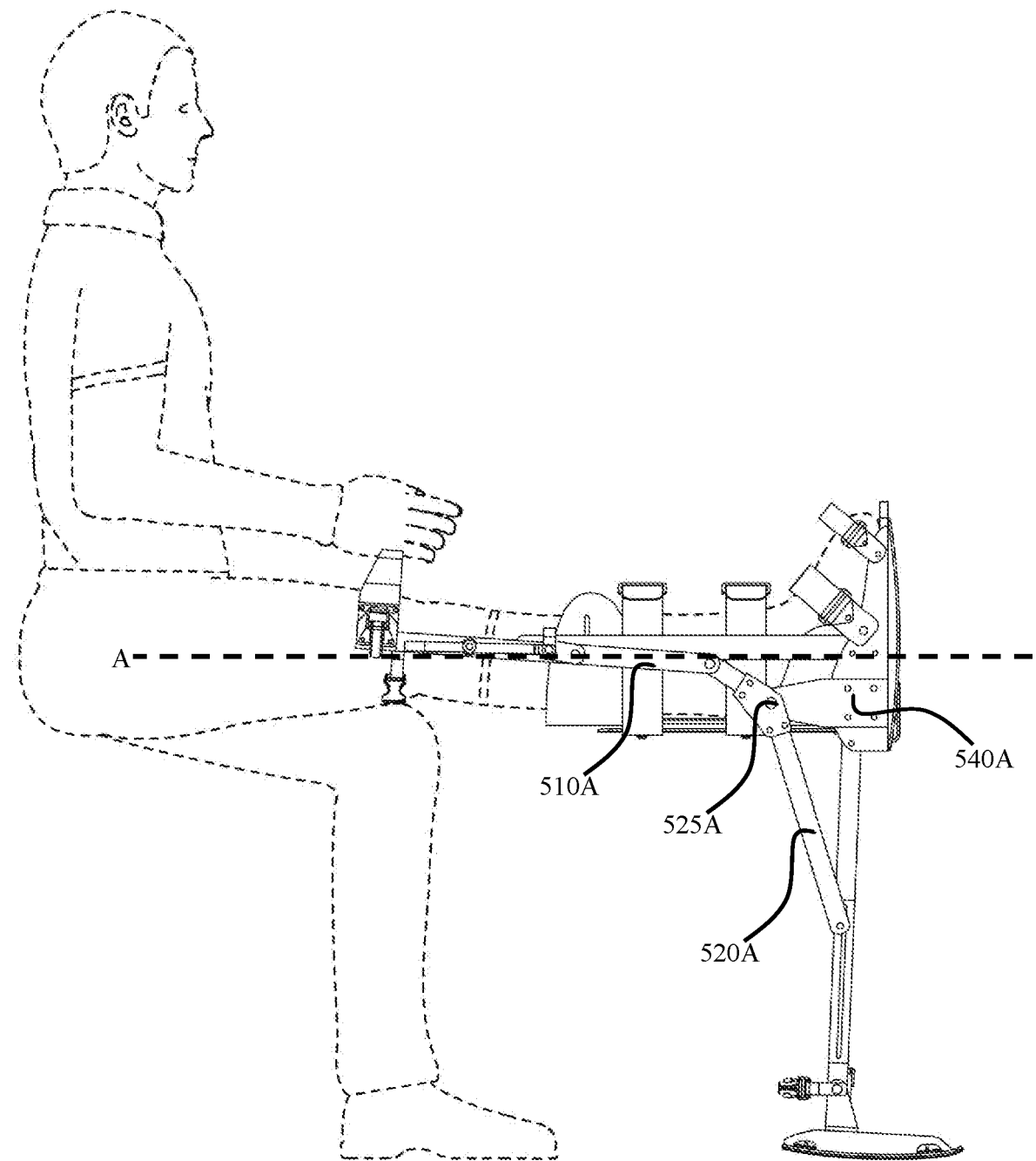
FIG. 3 illustrates the device for supporting a lower limb in accordance with an embodiment of the present invention shown in FIG. 1, when the limb support is in the extended position, in situ.

As depicted in FIGS. 3 and 4, the driving mechanism 500A also includes a restraining plate 540A secured to and extending from the side of the foot portion 121A of the housing. The second elongate member 520A is pivotably connected to the free end of the plate at the bend 525A between the first 523A and second 524A portions. The restraining plate 540A mechanically supports each of the first and second elongate members when the limb support 200 is in the extended position and prevents unnecessary lateral movement of the driving mechanism 500A while the limb support 200 is moved from the retracted to extended positions.

The relative dimensions of the first and second elongate members of the driving mechanism, the position of the plate along each side of the foot portion and slot length of the limb support have been selected such that the second end of the limb support fits closely to the housing in the retracted position of the limb support and that the limb support extends substantially perpendicularly to the housing to support the lower limb in the extended position.

Each side of the limb support 200A, 200B is releasably connectable to the adjacent respective side of the first part of the driving mechanism 510A, 510B via a fastener 280A, 280B. As shown in FIG. 6, the fastener 280A is a side release buckle including a receiving portion 281A and an engaging portion 282A. The engaging portion 282A for each buckle is attached to the limb support 200A to an end of the end portion of the bridge 256A. The receiving portion 281A for each buckle is attached to the first part of the driving mechanism under and adjacent the handle 550. This location of the fastener 280A makes it easy for the user to reach and unbuckle the fastener 280A while wearing the device 1000.

It is envisaged that a variety of different types of fasteners can be used to secure the limb support to the first part of the driving mechanism in the retracted position of the limb support.

Each part of the driving mechanism 500A, 500B also includes a driving mechanism lock 570A, 570B to prevent movement of the first part of the driving mechanism 510A, 510B relative to the housing 100 to ensure that the limb support 200 is locked in the extended position.

As can be seen for example, in FIG. 5, each side of the driving mechanism 500A, 500B is configured such that the first elongate member 510A, 510B is parallel to and adjacent the arms of the leg portion of the housing 111A, 111B.

The driving mechanism lock 570B includes a longitudinally extending box 571B with an internal cavity (not shown) and a longitudinally extending slot 573B that is contiguous with the internal cavity 572B. The box 571B is fixed to an inner surface of the first elongate member 510B with the slot 573B facing the inner surface of the first elongated member.

It is envisaged that in another embodiment (not shown), the first elongated member may include the internal cavity and the longitudinally extending slot. In this embodiment (not shown), a separate box is not required.

There is a polyurethane roller 574B attached to an outer surface at the top end of the arm 111B. The polyurethane roller 574B is located within and moveable along the internal cavity along the longitudinally extending slot 573B. The slot 573B is sized that the roller 574B is retained within the internal cavity.

The driving mechanism lock 570B further comprises a removeable stopper 575B attached to the outer side of first elongate member 510B of the driving mechanism. There is a window 576B located at and extending through a front facing surface of the box. One end of the cavity is located adjacent the handle and the other end of the cavity is located at a point along the length of the first member 579A. The window 576A is located above the other end of the internal cavity.

The stopper 575B is made of metal bent into a U-shape. Therefore, the stopper has a first end 577B and a second end 578B separated by a bend. A first moveable member 579B is attached to and pivotably moveable relative to the external surface of the first elongate member of the driving mechanism 510A. The first moveable member has a first end 580B and a second end 581B. A second moveable member 582A has a first end 583B, and a second end 584B fixed to the external surface of the first elongate member of the driving mechanism 510B.

Figure 11:
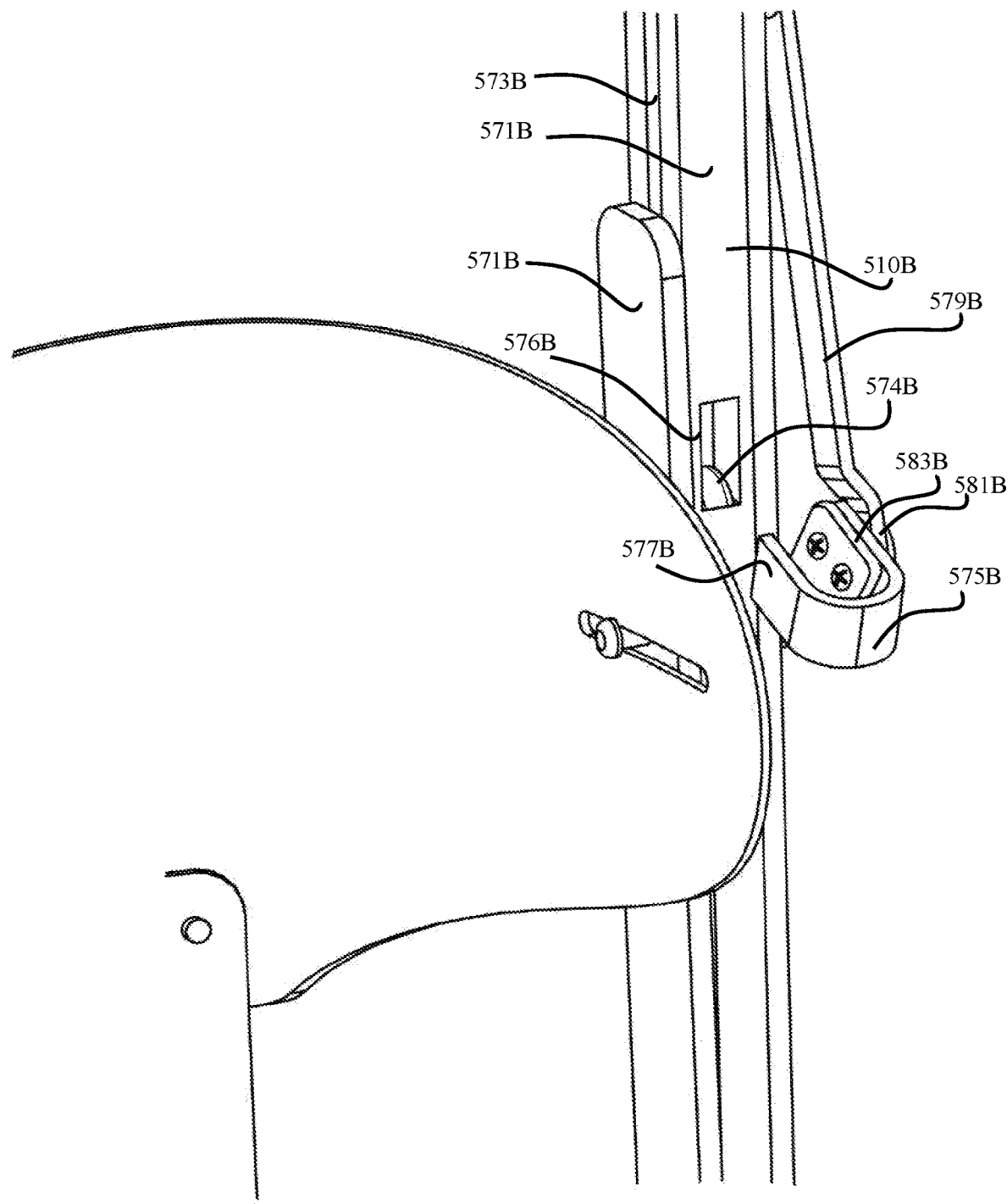
FIG. 11 is view of the driving mechanism lock in accordance with an embodiment of the present invention shown in FIG. 1.

The second end of the stopper 578B is located between and fixed to each of the second end of the first moveable member 581B and the first end of the second moveable member 579B as shown in FIG. 11.

The first moveable member 577B has an inflection 582B adjacent the second end of the first moveable member 581B configured such that the first moveable member 577B and the second moveable member 578B can fit parallel to each other when aligned vertically i.e. that the first end 583B can fit into the gap created by the inflection.

When the first part of the driving mechanism 510B is moved parallel to the limb to move the limb support 200B from a retracted to an extended position, the polyurethane roller 574B moves within the internal cavity and along the slot 573B. The box can be made of metal and sized to house the polyurethane roller. Advantageously, there is low friction between the polyurethane roller 574B and the metal of the box which enables smooth movement of the roller 574B within the cavity 572B.

The length of the slot 573B and cavity 572B are each configured such that the polyurethane roller 574B is at the top end of the longitudinal cavity 572B in the retracted position of the limb support. The slot 573B is also configured such that the polyurethane roller 574B located between the window 576B and the second end of the longitudinal cavity 575B in the fully extended position of the limb support 200.

Before the driving mechanism 500B is engaged to move the limb support 200B from the retracted to the extended position, the driving mechanism lock 570B is disengaged as shown in FIG. 11. When the limb support 200 is in the extended position, the user can push the unfixed end of the stopper 577B into the window 576B to prevent the polyurethane roller 574B moving towards handle 550 within the cavity 572B.

To engage the driving mechanism lock 570B, the user pushes the first end of the first moveable member 580B into vertical alignment with and into a position that is parallel to the outer surface of the first elongate member of the driving mechanism 510B. This causes the second end of the first moveable member 581B and the second moveable member 582B to also move into parallel alignment with the first part of the driving mechanism 510B. This also causes the first end of the stopper 577B to enter the window above the stopper 576B. In this position, the first end of the first moveable member 580B abuts with a horizontal surface 585B located under the end of the handle 551B such that any movement of the handle 550 towards the foot of the device 120 is prevented by the lock 570A.

The first end of the first moveable member 570A also has an outer rubber sleeve 586A to increase the friction between the horizontal surface 585A and the first end 580A so that the chance of the first end of the first moveable member 580A slipping relative to the horizontal surface 585A is reduced, for example, when the user pushes down on the handle 550 in a locked position of the driving mechanism 500A, 500B while the limb support 200 is in the extended position.

To disengage each driving mechanism lock 570A, 570B the user simply pushes the first end of the first moveable member 580A, 580B out of vertical alignment with or out of a position that is not parallel to the outer surface of the first part of the driving mechanism 510A, 510B. The second end of the first moveable member 581A, 582A moves away from the first part of the driving mechanism 510A, 510B and causes removal of the first end of the respective stopper 577A, 577B from the cavity through the respective window 576A, 576B.

The use of the device 1000 in accordance with the illustrated embodiment will now be described. Before the user wears the device 1000, the limb support 200 is in the retracted position and the limb support 200 is fastened to the first part of the driving mechanism 510A, 510B via the respective fastener 570A, 570B. The driving mechanism lock 570A, 570B is also disengaged.

The handle 550 is removed by disengaging the over-centre fasteners 560A, 560B located on either side of the handle 550 so that the handle 550 does not obstruct inserting the lower limb into the housing 100.

A user while seated on a chair or a bench for example, inserts their lower leg which is covered by an orthotic boot, foot first into the cavity of the housing device 110 while the limb support 200 is in the retracted position. The user can then secure their lower leg within the device 1000 by adjusting the straps until they feel their lower leg is secure within the device 1000. The user can then reattach the handle 550 to the first part of the driving mechanism 510A, 510B by aligning the first part of the alignment guide 591A, 591B on each side of the handle 550 with the second part of the alignment guide 592A, 592B on the first end of the first part of the driving mechanism 510 such that the protrusions are inserted into the recess, and engaging each loop of the over centre fastener with the respective retainer of the catch plate 561A.

The user can rest the leg while wearing the device 1000 on the ground. Once the lower leg is secured within the device 1000, the user unbuckles the buckle fastener 280A, 280B to disconnect the limb support 200 from the first part of the driving mechanism 510A, 510B. The user then pushes the limb support 200 away from the housing 100. The user then raises their lower limb and therefore, the device 1000 above the ground. This gives the user some space underneath their knee to manipulate the limb support 200.

The user unlocks the base 250 by holding down the first ends of both levers 410A, 410B and simultaneously moving the base 250 from the parallel position to a position perpendicular to the elongated brace 211A, 211B by rotating the base 250 about the elongate support 211A, 211B. The user then locks the base 250 in the perpendicular position by releasing the levers 410A, 410B until the second ends of the levers engage with the holes in each respective second end of elongated brace.

The user then grips the handle of the driving mechanism 550 and pulls it parallel to the longitudinal axis of the housing in a proximal direction (towards themselves) while extending their knee. Upon proximal movement of the handle 550, the first elongate member 110 translates along the lower limb and moves parallel to the arms of the housing, and the second elongate member simultaneously rotates approximately about the restraining plate. While the second elongate member rotates, the second end of the second elongate member translates along the slot from the first end of the slot to the second end of the slot. As the second elongate member is rigid, this movement of the second elongate member drives the elongate limb from the retracted position to the extended position. When the second end of the slot has traversed the entire length of the slot, the limb support is in the extended position.

In the extended position, the handle is at a position above the knee.

The driving mechanism lock is then engaged into the locked position to lock the limb support in position and to prevent movement of handle 550 in the opposition direction.

To return the limb support 200 to the retracted position, the driving mechanism lock 570A, 570B on either side of the device is disengaged and the user pushes on the handle. The second end of each second elongate member 522A, 522B moves from the second end of the slot back to the first end of the slot and pulls the limb support 200 towards the back of the housing. When the base 250 is sufficiently close, the user can readily grip the base 250, unlock the base lock 400 and fold the base 250 down into the position parallel to the limb support 200. The user can then connect the limb support 200 to the first part of the driving mechanism using each buckle 280A, 280B.

To remove the device, the user can remove the handle 550, loosen the straps 105 and then, carefully pull the device 550 off the lower limb.

The advantage of the mechanical driving mechanism illustrated in the embodiments is that it is simple, easy to use, robust and long-wearing. The user can use the device for an extended period of time such as for a number of years without having to maintain or replace the device.

Further, the position of the handle, buckle, base, base lock and driving mechanism lock are selected to be within reach of the user when they are seated and wearing the device, so that the user can easily and comfortably wear and deploy the device.

Advantageously, the buckle, base lock and driving mechanism lock in the illustrated embodiment do not require much manual dexterity or force to use. Therefore, the user will be motivated to use the device and to continue using the device to elevate their lower leg.

The driving mechanism, limb support, arms of the housing and other parts of the device which require strength and stiffness such as the plates on each side of the foot portion can be made of a suitable metal such as steel or aluminium. Alternatively, a suitably strong and stiff plastic may be used. In another embodiment, a composite material can be used such as a glass-reinforced plastic.

In other embodiments, other parts of the device can also be made of plastics with suitable mechanical properties.

The device is advantageously lightweight so that it is easy to carry and so that it does not unnecessarily load the injured lower leg while worn. The device is configured such that the user can walk with the device on the lower limb.

The device can be made in a number of sizes to suit different age groups and demographics of users.

It is envisaged that the foot portion of the housing can be constructed in a number of different ways such as molding using a suitable material such as types of plastics.

The skilled person will appreciate that pivotable connections between parts can be provided in a number of different ways including nuts and bolts with bearings to allow for the desired movement.

It is envisaged that the above device can be used to provide therapy for a variety of medical issues associated with a lower limb which require elevation of the lower limb such as fractures in the ankle, foot and shin, ankle sprains, achilles tendon injuries or calf muscle tears.

As mentioned above, the housing of the device can be modified to accommodate for different types of orthotics around the injured lower leg while still being comfortable for the user. For example, the housing can be modified so that a diabetic patient can comfortably wear the device while wearing normal shoes. For example, the padding housing can also be modified for a person wearing an orthotic boot, or plaster or a sand shoe or other shoes such as an ugg boot, for example.

It is envisaged that other parts of the device can be modified without departing from the scope of the invention.

Interpretation

Embodiments

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may do so. Furthermore, the particular features, structures or characteristics may be combined in any suitable manner, as would be apparent to one of ordinary skill in the art from this disclosure, in one or more embodiments.

Similarly it should be appreciated that in the above description of example embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description of Specific Embodiments are hereby expressly incorporated into this Detailed Description of Specific Embodiments, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Comprising and Including

In the claims which follow and in the preceding description of the invention, except where the context requires otherwise due to express language or necessary implication, the word "comprise" or variations such as "comprises" or "comprising" are used in an inclusive sense, i.e. to specify the presence of the stated features but not to preclude the presence or addition of further features in various embodiments of the invention.

Any one of the terms: including or which includes or that includes as used herein is also an open term that also means including at least the elements/features that follow the term, but not excluding others. Thus, including is synonymous with and means comprising.

Scope of Invention

Thus, while there has been described what are believed to be the preferred embodiments of the invention, those skilled in the art will recognize that other and further modifications may be made thereto without departing from the spirit of the invention, and it is intended to claim all such changes and modifications as fall within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

Although the invention has been described with reference to specific examples, it will be appreciated by those skilled in the art that the invention may be embodied in many other forms.

INDUSTRIAL APPLICABILITY

It is apparent from the above, that the arrangements described are applicable to the medical device and healthcare industries.

The invention claimed is:

1. A device for supporting a lower limb of a subject, comprising:
   a housing for a lower limb, the housing having a longitudinal axis configured to be aligned with a longitudinal axis of the lower limb, in use;
   a limb support comprising an elongated bracing member;
   a driving mechanism connected between the housing and the limb support, the driving mechanism comprising a first part attached to the housing and a second part connected to the limb support; and
   an actuator configured to be located at or near a knee of the subject wearing the device and connected to the driving mechanism for enabling the subject to operate the driving mechanism,
   wherein, in use, actuation of the driving mechanism drives a movement of the limb support between a retracted position parallel to the longitudinal axis of the housing and an extended position in which the limb support extends perpendicularly to the longitudinal axis of the housing to support the lower limb, and
   wherein in the extended position, the limb support is adapted to extend between the housing and the ground to support the lower limb above the ground.

2. The device of claim 1, wherein the housing includes a foot portion configured to house a foot of the subject.

3. The device of claim 2, wherein the housing includes at least two rigid arms, each rigid arm attached to a first and second side of the foot portion to support the lower limb, in use.

4. The device of claim 3, wherein the housing includes a supporting cover attached to each of the two rigid arms that covers a substantial part of a back of the lower leg of the subject, in use.

5. The device of claim 4, wherein the supporting cover is adjustable to accommodate for different sizes of lower limb of the subject.

6. The device of claim 2, wherein the foot portion has a convex bottom surface comprising a gripping material.

7. The device of claim 2, wherein the foot portion includes a stabilizing portion extending from the bottom surface, the stabilizing portion being configured to keep the device upright when the subject is not wearing the device.

8. The device of claim 1, wherein the limb support comprises a base pivotally connected to the elongated bracing member.

9. The device of claim 8, wherein the limb support further comprises a base lock to lock the base in a position substantially perpendicular to the elongated bracing member when the limb support is in the extended position.

10. The device of claim 8, wherein the base has a convex lower surface.

11. The device of claim 1, wherein the driving mechanism comprises the first part comprising a first elongate member, the first elongate member including a first end and a second end,
    wherein the driving mechanism further comprises the second part comprising a second elongate member, the second elongate member including a first end and a second end, the second end of the first elongate member pivotably connected to the first end of the second elongate member, and
    wherein the actuator is a handle fixed to the driving mechanism for the subject to grip to move the first part of the driving mechanism in a direction parallel to the longitudinal axis of the housing to drive the limb support between the retracted position and the extended position.

12. The device of claim 11, wherein the handle is detachable.

13. The device of claim 11, wherein the actuator drives the first elongate member which interacts with a slide to allow the first elongate member to be driven substantially along the housing, and
    wherein the second end of the second elongate member slides in a captured manner in a linear recess in the elongated bracing member of the limb support to enable the limb support to stably move between the retracted position and the extended position.

14. The device of claim 1, wherein the elongated bracing member comprises a guide extending along at least part of a length of the elongated bracing member, the guide being configured to engage with the second part of the driving mechanism.

15. The device of claim 14, wherein the guide comprises a cavity, and
    wherein the device further includes a roller attached to a second end of a second elongate member, the roller being located within and moveable along the cavity of the elongated bracing member, and moveable along the guide of the elongated bracing member.

16. The device of claim 1, wherein the housing includes a leg portion configured to house a leg of the subject.

17. The device of claim 1, wherein the housing includes adjustable straps configured to secure a lower leg of the subject within the housing.

18. The device of claim 1, wherein the device further includes a fastener connected between the limb support and the housing to fasten the limb support to the housing when the limb support is in the retracted position.

19. The device of claim 1, wherein the device further comprises a driving mechanism lock to prevent movement of the first part of the driving mechanism relative to the housing when the limb support is in the extended position or in the retracted position.

* * * * *